(12) United States Patent
Blank

(10) Patent No.: US 7,789,906 B2
(45) Date of Patent: Sep. 7, 2010

(54) METAL STRUCTURE COMPATIBLE WITH MRI IMAGING, AND METHOD OF MANUFACTURING SUCH A STRUCTURE

(75) Inventor: Thiemo Arnim Blank, Plankstadt (DE)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 10/507,347

(22) PCT Filed: Mar. 14, 2003

(86) PCT No.: PCT/EP03/02708

§ 371 (c)(1), (2), (4) Date: Jan. 11, 2006

(87) PCT Pub. No.: WO03/075797

PCT Pub. Date: Sep. 18, 2003

(65) Prior Publication Data

US 2006/0173529 A1 Aug. 3, 2006

(30) Foreign Application Priority Data

Mar. 14, 2002 (GB) .................................. 0206061.4

(51) Int. Cl.
A61F 2/06 (2006.01)
(52) U.S. Cl. ....................................................... 623/1.16
(58) Field of Classification Search ................. 623/1.11, 623/1.15, 1.16
See application file for complete search history.

(56) References Cited

U.S. PATENT DOCUMENTS 4,661,530 A 4/1987 Gogolewski et al.

(Continued)

FOREIGN PATENT DOCUMENTS

EP 1 023 609 B1 6/2001

(Continued)

OTHER PUBLICATIONS

Adam, MD et al., "Interventional Magnetic Resonance Angiography", Seminars in Interventional Radiology, vol. 16, No. 1, (1999), pp. 31-37.

(Continued)

Primary Examiner—Anhtuan T Nguyen
Assistant Examiner—Sarah A Simpson
(74) Attorney, Agent, or Firm—Rutan & Tucker, LLP

(57) ABSTRACT

The present invention relates to tubular radially expansible metal structures, having an abluminal wall, a luminal wall and a radial wall thickness therebetween with struts defining through-apertures in the wall, the structure further defining a plurality of expansible rings arranged adjacent one another along the longitudinal axis of the structure, each of the rings defining at least one bridge strut, and adjacent rings being linked by a bridge extending between adjacent bridge struts on adjacent rings. The bridges, a plurality of which are distributed throughout the length of the tubular structure and are configured and arranged to divide the tubular structure into axially spaced and electrically insulated sections, advantageously exhibit reduced electrical conductivity throughout their wall thickness. The present invention relates furthermore to a method of manufacturing such a tubular structure, as well as a method of visualizing a bodily lumen supported by such a tubular structure deployed therein.

35 Claims, 5 Drawing Sheets

U.S. PATENT DOCUMENTS

| | | | |
|---|---|---|---|
| 4,830,003 | A | 5/1989 | Wolff et al. |
| 5,122,154 | A | 6/1992 | Rhodes |
| 5,123,917 | A | 6/1992 | Lee |
| 5,320,100 | A | 6/1994 | Herweck et al. |
| 5,599,311 | A | 2/1997 | Raulerson |
| 5,630,829 | A | 5/1997 | Lauterjung |
| 5,725,572 | A | 3/1998 | Lam et al. |
| 5,733,326 | A | 3/1998 | Tomonto et al. |
| 5,741,327 | A * | 4/1998 | Frantzen .................... 623/1.34 |
| 5,807,241 | A | 9/1998 | Heimberger |
| 5,860,999 | A | 1/1999 | Schnepp-Pesch et al. |
| 5,951,458 | A * | 9/1999 | Hastings et al. ................ 600/3 |
| 6,083,259 | A | 7/2000 | Frantzen |
| 6,117,167 | A | 9/2000 | Goicoechea et al. |
| 6,123,722 | A * | 9/2000 | Fogarty et al. ............... 623/1.1 |
| 6,156,064 | A | 12/2000 | Chouinard |
| 6,159,239 | A | 12/2000 | Greenhalgh |
| 6,168,619 | B1 | 1/2001 | Dinh et al. |
| 6,176,875 | B1 | 1/2001 | Lenker et al. |
| 6,183,508 | B1 | 2/2001 | Stinson et al. |
| 6,183,509 | B1 | 2/2001 | Dibie |
| 6,221,099 | B1 | 4/2001 | Andersen et al. |
| 6,221,100 | B1 | 4/2001 | Strecker |
| 6,221,102 | B1 | 4/2001 | Baker et al. |
| 6,224,625 | B1 | 5/2001 | Jayaraman |
| 6,228,111 | B1 | 5/2001 | Tormala et al. |
| 6,231,516 | B1 | 5/2001 | Keilman et al. |
| 6,240,616 | B1 | 6/2001 | Yan |
| 6,241,691 | B1 | 6/2001 | Ferrera et al. |
| 6,251,136 | B1 | 6/2001 | Guruwaiya et al. |
| 6,270,524 | B1 * | 8/2001 | Kim .......................... 623/1.15 |
| 6,280,385 | B1 | 8/2001 | Melzer et al. |
| 6,325,822 | B1 | 12/2001 | Chouinard et al. |
| 6,350,279 | B1 | 2/2002 | McGuinness |
| 6,540,777 | B2 | 4/2003 | Stenzel |
| 6,565,599 | B1 | 5/2003 | Hong et al. |
| 6,673,107 | B1 * | 1/2004 | Brandt et al. .............. 623/1.35 |
| 6,712,844 | B2 * | 3/2004 | Pacetti ...................... 623/1.15 |
| 6,749,629 | B1 | 6/2004 | Hong et al. |
| 6,776,794 | B1 | 8/2004 | Hong et al. |
| 6,805,707 | B1 | 10/2004 | Hong et al. |
| 2002/0188345 | A1 | 12/2002 | Pacetti |
| 2004/0093075 | A1 | 5/2004 | Kuehne |
| 2004/0122506 | A1 | 6/2004 | Shanley et al. |
| 2004/0172128 | A1 | 9/2004 | Hong et al. |
| 2004/0249440 | A1 | 12/2004 | Bucker et al. |
| 2005/0049686 | A1 | 3/2005 | Gray et al. |
| 2005/0049688 | A1 | 3/2005 | Gray et al. |
| 2006/0136039 | A1 | 6/2006 | Martin |
| 2007/0168016 | A1 | 7/2007 | Gronemeyer et al. |

FOREIGN PATENT DOCUMENTS

| | | |
|---|---|---|
| JP | 2001520057 | 10/2001 |
| WO | WO-9628115 | 9/1996 |
| WO | WO-9633672 | 10/1996 |
| WO | WO 9638083 | 12/1996 |
| WO | WO-9910035 A2 | 3/1999 |
| WO | WO 99/19738 | 4/1999 |
| WO | WO 99/43378 | 9/1999 |
| WO | WO 00/15151 | 3/2000 |
| WO | WO 01/01888 | 1/2001 |
| WO | WO 01/32102 A1 | 5/2001 |
| WO | WO-0215820 | 2/2002 |
| WO | WO 02/053066 | 7/2002 |
| WO | WO-02047575 | 7/2002 |
| WO | WO 03/015662 A1 | 2/2003 |
| WO | WO-03075797 | 9/2003 |
| WO | WO-2004071353 A2 | 8/2004 |

OTHER PUBLICATIONS

Amano et al., "Metallic Artifacts of Coronary and Iliac Arteries Stents in MR Angiography and Contrast-Enhanced CT", Clin Imaging 1999; 23: 85-89.

Bakker et al., "MR-Guided Balloon Angioplasty: In Vitro Demonstration of the Potential of MR For Guiding, Monitoring, and Evaluating Endovascular Interventions", JMRI, 8:245-250 (1998).

US FDA Center for Devices and Radiological Health Magnetic Resonance Working Group, "A Primer on Medical Device Interactions With Magnetic Resonance Imaging System", <http://www.fda.gov/cdrh/ode/primerf6.html>, Mar. 5, 2000.

Mar. 20, 2009 Japanese Examination Report issued in Japanese application 2003-574075.

Mar. 18, 2009 Canadian Examination Report issued in Canadian application 2,478,709.

Sep. 3, 2009 Non-final Office Action in U.S. Appl. No. 10/585,722, filed Jun. 26, 2008.

* cited by examiner

METAL STRUCTURE COMPATIBLE WITH MRI IMAGING, AND METHOD OF MANUFACTURING SUCH A STRUCTURE

CROSS-REFERENCE TO RELATED APPLICATIONS

This is a U.S. national stage of International Application PCT/EP03/02708, filed on Mar. 14, 2003, which claims priority to UK Patent Application No. 0206061.4, filed on Mar. 14, 2002, the disclosures of which are incorporated herein by reference in their entirety.

FIELD OF THE INVENTION

This invention relates to magnetic resonance imaging of a metal structure, and in particular, but not exclusively, to a tubular radially expansible metal structure, and in particular to such a tubular metal structure which defines a plurality of expansible rings arranged adjacent one another along the longitudinal axis of the structure, and in which each of the rings defines at least one bridge end and adjacent rings being linked by a bridge extending between adjacent bridge ends on adjacent rings. The invention also relates to a method of manufacturing such a tubular metal structure, and to a method of visualising a lumen supported by such a tubular metal structure using a MRI-technique.

The present invention has particular usefulness for providing tubular structures in the form of medical stents, irrespective of whether they are self-expandable or balloon-expandable, made of a surgical grade material, such stainless steel, cobalt or nickel-titanium alloy. In addition it also has applications to implants (for example filters and fluid-flow measuring devices) other than stents. It may also have applications outside the field of medical stents, implants and prostheses. It is particularly of interest for laser-cut prostheses and self-expanding nickel-titanium alloy devices.

BACKGROUND ART

With the advent of magnetic resonance imaging (MRI) techniques, the imaging of soft tissue structures in a non-invasive fashion has become feasible. When a human or animal body is exposed to a strong external time-independent magnetic field ($B_0$), the magnetic moments associated with the spins of the exposed atomic nuclei will become aligned with the direction of $B_0$-field resulting in a total magnetisation to be detected. The direction of this total magnetisation in its equilibrium state is parallel to the direction of the external magnetic field $B_0$. This equilibrium state, however, is not static but, rather, dynamic because the total magnetisation precesses with the so-called Larmor-frequency about the direction of the $B_0$-field.

Upon application of a high frequency (HF) signal having a frequency equal to the Larmor-frequency (resonance frequency) and emerging from a direction different to that of the $B_0$-field, a spin-flip of the nuclei can be observed and associated with the spin-flip, the relaxation time required to relax the spins back to their original alignment with the $B_0$-field can be measured by means of an external coil being tuned in resonance with the HF-signal.

The angle $\alpha$ by which the spins have been deflected by the HF-signal with respect to the $B_0$-field direction is proportional to the time period of the HF-signal and the magnitude of the static magnetic field $B_0$. Subsequent to the spin flip, the total magnetisation precesses about the $B_0$-field with the angle $\alpha$, and this precessing motion of the total magnetisation may be recorded by the external coil that is oriented perpendicular to the $B_0$-field. The coil outputs a voltage signal whose magnitude is proportional to $\sin(\alpha)$, is proportional to the density of the spins and is inversely proportional to the temperature.

If the spins are deflected by an angle $\alpha$ of 90°, a maximum signal response is obtained. Due to the individual spins losing their strict phase-correlation, the recorded signal amplitude decreases exponentially with the relaxation time $T_2$. Simultaneously, the total magnetisation increases exponentially again in the direction of the $B_0$-field towards the equilibrium magnetisation with the relaxation time $T_1$. By means of magnetic gradient-fields switched on at the correct point in time, it is possible to image the two relaxation times in a grey scale encoded image with spatial resolution.

With the discovery of superconductors having a transition temperature above liquid nitrogen temperature, superconducting magnets have become widely used, and thus have rendered MRI-imaging techniques more cost-effective. MRI imaging techniques have so far been predominantly used for imaging soft tissue structures, such as the human brain and other internal organs.

Implants, such as vascular grafts or stents, are predominantly made of biocompatible metals. These metals are still preferred over their polymeric-based competitors. Nickel-titanium alloys are attractive in that they have good fatigue resistance and a memory which brings them to the shape desired upon deployment. Stainless steel or cobalt alloys are other biocompatible materials used for making stents.

There has long been a wish to determine the rate of fluid-flow through the stent lumen as well as the amount of tissue hyperplasia in order to examine the extent of restenosis in each patient during follow-up examinations at intervals after the stent has been implanted. This information would also help stent designers to optimise and improve their stent structures in terms of avoiding restenosis from occurring as well as to help the medical practitioner to exactly determine the extent to which restenosis inside the stent lumen re-occurs after it has been deployed inside the human or animal body in order to specify more precisely those measures for treating the restenosed region in an appropriate and timely manner.

Attempts to MRI-image the blood flow and tissue-ingrowth in the vicinity of a metallic vascular implant are frustrated, or at least impaired, by the ferromagnetic or paramagnetic characteristics of the materials of the implant, which result in artefacts in the images, which reduce the quality of these images down to levels too low to be useful.

On the one hand, these artefacts are thought to be due to differences in susceptibility between metal and tissue resulting in magnetic fields in proximity of the metallic implant being non-uniform and multidirectional, thus destroying the signal response from the HF-pulse in the proximity of the implant. On the other hand, the wavelength of the HF-signals used is such that the implant is, to a certain degree, impenetrable to the HF-signal, i.e. the penetration of the HF-signal through the implant is impaired. Hence, the image of the implant lumen or the body structure therein has been seriously compromised.

These disadvantages reduce the effectiveness of MRI-imaging techniques for imaging patency of vascular metallic implants, and consequently, X-ray fluoroscopy with all its known disadvantages (invasive, ionising radiation) is used instead.

WO-A-96/38083 discloses a probe having at least one pair of elongated electrical conductors, preferably disposed parallel to each other within a dielectric material, and having a pair of ends electrically connected to each other. This probe thus formed is, in a preferred use, introduced into small blood vessels of a patient to facilitate determination of arteriosclerotic plaque using an MRI-imaging technique. This probe, however, is electrically conductive along its entire axial length, thus providing a Faraday screen to minimize dielectric losses between the probe and the surrounding material.

U.S. Pat. No. 6,083,259 addresses the problem of poor visibility of a lumen within a stent. The stents it discloses generally include a series of co-axially aligned circumferential elements and oriented in separate planes spaced axially from each other. Each circumferential element includes a wave-like series of curvatures. Each curvature includes a trough, defined as being that portion of each circumferential element which is most distant from an adjacent circumferential element, and a crest, being defined as that portion of each circumferential element that is closest to an adjacent circumferential element. Each gap between two adjacent circumferential elements is spanned by at least one axial element. The axial elements are either tie bars or double-bend links, such as a S-shaped link. Both the stent and the axial elements are made of the same material. The stent can additionally include enhanced density markers which increase the visibility of portions of the stent when viewed with a medical imaging device, such as a fluoroscope.

U.S. Pat. No. 5,123,917 discloses an intraluminal vascular graft in which separate scaffold members are sandwiched between two PTFE inner and outer tubes. The ring-like scaffold members are made of stainless steel and are expandable upon application of a radially outwardly extending force from the interior of the inner tube. The vascular graft includes no metallic cross-links adjoining two adjacent scaffold members. It is the PTFE inner and outer tubes which hold the vascular graft together.

Another intraluminal graft for placement in a body lumen is disclosed in U.S. Pat. No. 5,122,154. The graft comprises a plurality of stents which may be completely encased in the graft material, the graft material preferably being made of PTFE. In this intraluminal graft, the individual stents are spaced apart axially. The only link between adjacent stents is the PTFE graft material.

EP-A-1 023 609 discloses a stent, said to be compatible with MRI-imaging techniques. The stent has a structural skeleton, which is provided with metal coating portions that function as an inductor and a capacitor. Here, the inductor and capacitor may be co-terminous with the skeleton itself, or may be separate devices attached to the skeleton which are linked in parallel to one another. The inductor and capacitor represent a harmonic oscillator which is tuned in resonance with the HF-signal of a MRI-imaging apparatus.

In case of the skeleton being co-terminous with the inductor and the capacitor, the stent may consist of a structure of two or more layers, in which the first layer is the skeleton, made up of a material having a relatively low electrical conductivity, such as titanium alloys, plastics or carbon fibres, and the coating is a second layer having a very high electrical conductivity in comparison with the first layer and representing the inductor and capacitor material, for example gold or silver. The second, highly conductive layer is cut along circumferential paths during manufacture of the stent. This way, the stent structure comprises several inductors which are connected in parallel. The capacitor is formed at one end of the stent structure by cutting through the highly conductive layer along a relatively short axial path being perpendicular to the cutting paths forming the inductors. In operation, an amplification of the excitation of the nuclei spins by means of the resonance circuit, i.e. the inductor and capacitor, is induced. Therefore, position determination of the stent may be achieved. Furthermore, based on the different excitations inside and outside of the stent, flow rate measurements of the medium flowing through the stent or along the stent can be performed. In the structural skeleton of the stent itself, that is, the first layer, there are no struts in the mesh-structure of the stent which exhibit portions of decreased conductivity, or are entirely severed so that gaps in the mesh-structure would appear. The only gaps are in the second layer for imparting to the stent the property of an harmonic oscillator.

WO-A-01/32102 discloses a tubular structure having a plurality of meander-shaped rings.

In U.S. Pat. No. 5,807,241 a bendable endoscope is disclosed which comprises tube sections so that neighbouring tube sections are completely materially separated from one another via circumferential separating gaps and are only connected to one another by means of a positive fit. By providing an appropriate number of tube sections, a flexible shaft may be formed. The manufacture may be effected by laser-cutting from a rigid tube.

U.S. Pat. No. 5,741,327 discloses a radially expandable surgical stent with radiopaque marker elements in the form of rings attached to the ends of the stent. The radiopaque marker elements include tabs which match the contour of receivers provided at both ends of the stent for secure attachment.

An expandable metallic stent said to be MRI-compatible is disclosed in published US application no. 2002/0188345 A1. The stent has discontinuities of non-conducting material. These eliminate electrically conducting paths in the stent rings. This makes the stent easier to image with MRI. The non-conducting material can include various materials, such as adhesives, polymers, ceramics, composites, nitrides, oxides, silicides and carbides. The discontinuity is preferably shaped that during expansion the discontinuity is placed in primarily a compressive stress. The discontinuities are advantageously placed circumferentially along the stenting rings.

SUMMARY

It is an object of the present invention to provide a tubular metal structure, such as a stent, which allows MRI-imaging of the lumen within the tubular metal structure. It is also another object of the present invention to provide a tubular structure which permits improved determination of the fluid-flow through the lumen of the structure by means of MRI-imaging.

This object is solved by a tubular metal structure having the features of independent claim 1. Further embodiments are described in dependent claims 2 to 19.

Another object of the invention is to provide a method of manufacturing such a tubular structure.

This object is solved by a method defined in claim 20. Optional or preferred features of the method are subject of dependent claims 21 to 23.

Another object of the invention is to provide a method of visualising a stented lumen using a MRI-technique. This object is solved by a method defined in claim 24.

According to one preferred embodiment of the tubular metal structure of the present invention, the bridges linking two adjacent meander-shaped rings together, comprise complementary mating portions as the portion of reduced conductivity. In case that these mating portions are of the type of male/female form-fitting portions, a rapid connection between two adjacent rings can be accomplished, either manually or by means of a specifically designed machine tool. In another preferred embodiment, these form-fitting portions may have a frusto-conical shape. If the stent material is cut by a laser with its line of action always being radial to the stent cylinder, a frusto-conical form-fit between the two complementary form-fitting portions is achieved, thereby enhancing the security of attachment and the precision of placement of both complementary form-fitting portions.

In accordance with another preferred embodiment, at least one of the mating portions is encapsulated in a bio-compatible adhesive having poor electrical conductivity for enhancing the rigidity of the bridge and for providing a portion of reduced conductivity. This bio-compatible adhesive increases the maximum tensile force the bridge is capable to withstand upon radial expansion of the tubular structure and inhibits the current flow from one end of the implant to the other.

If, according to another advantageous embodiment, at least one of the mating portions comprises an oxide layer as the portion of reduced conductivity, the bio-compatible adhesive does not necessarily have to be non-conductive. The oxide layer can either be created, as described below, or can be the naturally occurring oxide layer on the surface of the metal.

An oxide layer as the portion of reduced conductivity is preferred due to the ease of creating the oxide layer on at least one of the mating portions. One way of creating the oxide layer is to radiate one of the mating portions with a laser, thus oxidising the metal surface of that mating portion. Another way is to immerse one of the mating portions in an oxidising agent, such as a Lewis acid, or subject it to an anodic oxidization process. If the temperature generated during laser-cutting is sufficiently high, then oxidisation may already take place during the laser-cutting step so that the above-described extra steps, e.g. immersing one of the mating portions into an oxidising agent or subjecting it to an anodic oxidization process, may be omitted. Depending on the magnitude of the voltage induced by the time-dependent magnetic field in the meander-shaped rings, a very thin oxide layer may be sufficient; such as the naturally occurring oxide layer on the surface of the metal or a very thin oxide layer created as described above, to prevent current-breakthrough between two mating portions forming the bridge. If the voltage exceeds a certain level, the addition of a non-conductive adhesive may well be suitable to prevent such current-breakthrough.

The exact shape of the outline of each of the mating portions, and the exact shape of the abutment surfaces on them which contact each other, is a matter of design freedom and choice. At the moment, for tubular structures which are stents, it is contemplated to provide the two mating portions as two complementary form-fitting portions one of which is the male mating portion with a mating head portion, and the other one of which is the female mating portion with an arcuate portion, such that the female mating portion comprises a rebated internal abutment surface to receive the corresponding mating head portion.

If the two complementary form-fitting portions forming the bridge are created by a laser-cutting process, in which the laser beam lies on a radius to the cylindrical form of the workpiece, the two mating portions automatically comprise a frusto-conical shape, which further provides a snap-fit inter-engagement of the two mating portions, further helping to accomplish precise positioning and orientation of the two mating portions relative to the tubular structure. Further, if the co-operating surfaces of the two mating portions are both cut with a laser on a radial line of action, then there will tend to be a self-centering and self-aligning effect when one meander-shaped ring is offered up, end-to-end, to the adjacent meander-shaped ring, particularly with self-expanding stent designs.

If a steerable laser is used for laser-cutting, the two form-fitting portions forming the bridge may be shaped such, that they are inter-locked with each other against inadvertant separation in use, either radially or axially, yet they are separated themselves by a film of oxide. This can be accomplished by varying an angle of tilt of the laser focus, as one advances the laser beam around the circumference of the connecting portions of two adjacent rings. By doing this, one can create, for example, cuts through the wall thickness which exhibit two frusto-conical zones in one of which the cone tip lies on the axis of the stent cylinder and in the other the cone tip lies outside the stent cylinder, such that the connecting portions are interlocked and not separable. This resembles a jig-saw with alternating tilted abutment surfaces. Due to the laser focus having a certain width, there is a gap between two adjacent bridge ends of the bridge providing sufficient room for the portion of reduced conductivity therebetween.

It is to be noted that the same effect can be achieved by appropriate emboss preparation of both form-fitting portions when the form-fitting portions were previously cut with a laser on a radial line of action. The emboss preparation aims to impart tilted surfaces on the two form-fitting portions.

In another advantageous embodiment, the length axis of the bridge is not parallel to the longitudinal axis of the tubular structure. Such a bridge with its axis not being parallel to the longitudinal axis of the tubular structure can give the overall structure enhanced flexibility, particularly when the structure is confined within an outer sheath and is advanced along a tortuous path within a body lumen. According to other embodiments of the present invention, the bridge may be meander-shaped or S-shaped for the same reasons.

A particular advantageous embodiment provides a tubular structure whose number of bridges is less than the number of meanders in one circumferential ring. In finding an improved structure well suited for MRI-imaging techniques, one can choose to reduce the number of bridges between two adjacent rings down to a structural minimum.

A practical minimum number of bridges between adjacent rings may be as low as 2 per circumference. The number, however, may depend on the mesh-structure of the tubular structure and whether the structure is self-expandable or ballon-expandable. The mechanical requirements on the mesh structure of a self-expandable stent vary from those of a balloon-expandable stent due to the stress-strain distribution within the mesh structure of the stent. Progressive release of a self-expandable stent by proximal withdrawal of an outer confining sheath creates a travelling zone of enhanced stress in the stenting material as the sheath travels along the length of the stent. This is to be compared with a uniform radial expansion by inflation of a balloon within the lumen of the stent. For balloon-expandable stents, there may not be a restriction on the minimum number of bridges between adjacent stenting rings. The number of bridges, however, can be chosen according to the mechanical requirements on the stent, such as flexibility required for ease of advancing the stent to the stenting site.

In another preferred embodiment, the meander-shaped rings exhibit a zig-zag shape. The zig-zag shape of the rings offers good radial elasticity of the tubular structure. Upon release of a self-expanding tubular structure out of an outer confining sheath, the zig-zag shape can relax to an expanded diameter. Along with this expansion goes improved flexibility of the tubular structure against the radially inwardly directed pressure from the surrounding bodily tissue in the installed configuration of the structure.

One supposes that the HF-signal is more likely to penetrate the metallic tubular structure because the tubular structure is no longer seen by the HF-signal as a Faraday cage, and therefore the HF-signal will also cause a spin-flip of the nuclei within the lumen of the tubular structure. Hence, one supposes, less artefacts will occur in the obtained MRI-image of the lumen, thereby facilitating imaging of the matter, such as tissue within the lumen of a body vessel, within the lumen of the tubular structure and determination of fluid-flow therethrough.

According to the second aspect of the present invention, there is provided a method of manufacturing a tubular radially expansible metal structure, the method comprising the steps of:

forming a plurality of expansible rings so that the rings are arranged adjacent one another along the longitudinal axis of the structure, and that each of the rings define at least one bridge strut;

forming bridges between adjacent rings by approximating respective bridge struts of adjacent rings;

characterised by the step of furnishing the bridges between each ring and its adjacent ring with reduced electrical conductivity throughout the wall thickness, such that there are a plurality of bridges distributed throughout the length of the tubular structure, and arranged and configured to divide the tubular structure into axially spaced and electrically insulated sections.

Further embodiments of this method are subject of dependent claims 21 to 23.

According to a third aspect of the invention, there is provided a method of visualising a stented lumen using MRI-technique which is characterised by the step of selecting for stenting said lumen a stent which is formed of electrically insulated metal stenting rings.

For a better understanding of the present invention, and to show more clearly how the same may be carried into effect, reference will now be made, by way of example, to the accompanying drawings.

DETAILED DESCRIPTION OF A PREFERRED EMBODIMENT

Skilled readers will appreciate that the stent cylinder can be formed from seamless tubular material, or from flat sheet material rolled into a seamed tube.

Skilled readers will also be well aware that there have been a very large number of proposals for strut patterns in the tubular configurations of stents. Whereas FIG. 1 shows an expandable strut pattern in a form which is particularly preferred for the present invention, nevertheless any of the well known strut patterns will have points at intermediate portions of the stent cylinder where individual adjacent meander-shaped rings can be attached to one another.

Figure 1:
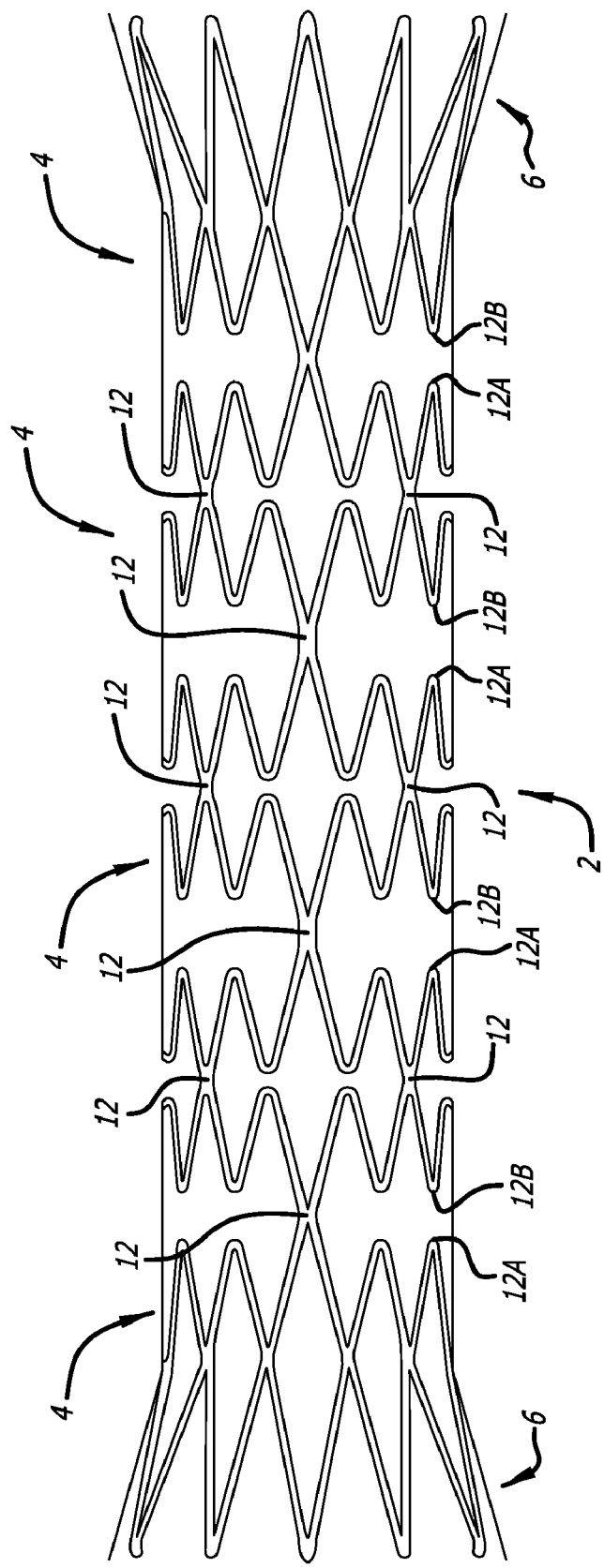
FIG. 1 is a side elevation of a tubular self-expanding stent structure along a line which intersects the long axis of the tube and is perpendicular to it, the stent being in its larger radius deployed configuration.

FIG. 1 shows a stent cylinder in the large radius configuration. As can be seen in FIG. 1, the stent cylinder 2 is constituted by a succession of struts which zig-zag their way around the full circumference of each individual ring 4. There is a vertex 12A, 12B where two successive struts intersect, and at some of which adjacent meander-shaped rings 4 are joined. Albeit FIG. 1 shows a stent cylinder with flared ends 6 for better anchorage of the stent cylinder inside a body vessel, the present invention is not intended to be limited to stents with flared ends.

In the illustrated embodiment, the stent is made from Nitinol®, a nickel-titanium shape memory alloy. A variant of the stent, shown in FIG. 1, may comprise tantalum spoons at both axial ends thereof which help visualising the stent using fluoroscopy. See Applicant's WO 02/15820. In other embodiments, the stent could be made of stainless steel, or any other biologically compatible conducting material capable of performing a stenting function.

It is conventional to form the lattice pattern of Nitinol® stents by laser-cutting. Cutting the frusto-conical mating surfaces of the body portion of the stent is achieved by aligning the laser in the normal, i.e. radial direction, thus intersecting the long axis of the stent tube. Once the slits in the workpiece of the stent tube are cut, most but not all of the vertices axially connecting two adjacent rings of the stent tube are severed, and only a few remain connected in order to maintain an integral tubular stent structure. The smaller the number of connected vertices, the greater the potential the stent has to bend out of a straight line as it is advanced along a tortuous path to the site of stenting. In addition, the flexibility of the stent after deployment is increased as well.

As can be seen in FIG. 1, the bridges 12 connecting two adjacent vertices 12A, 12B at two ends of a stent ring 4 facing each other, have a non-zero length, which, in turn, renders the overall structure in a radially compressed configuration more flexible, so that it can be more easily advanced along a tortuous path within a body lumen.

Figure 2:
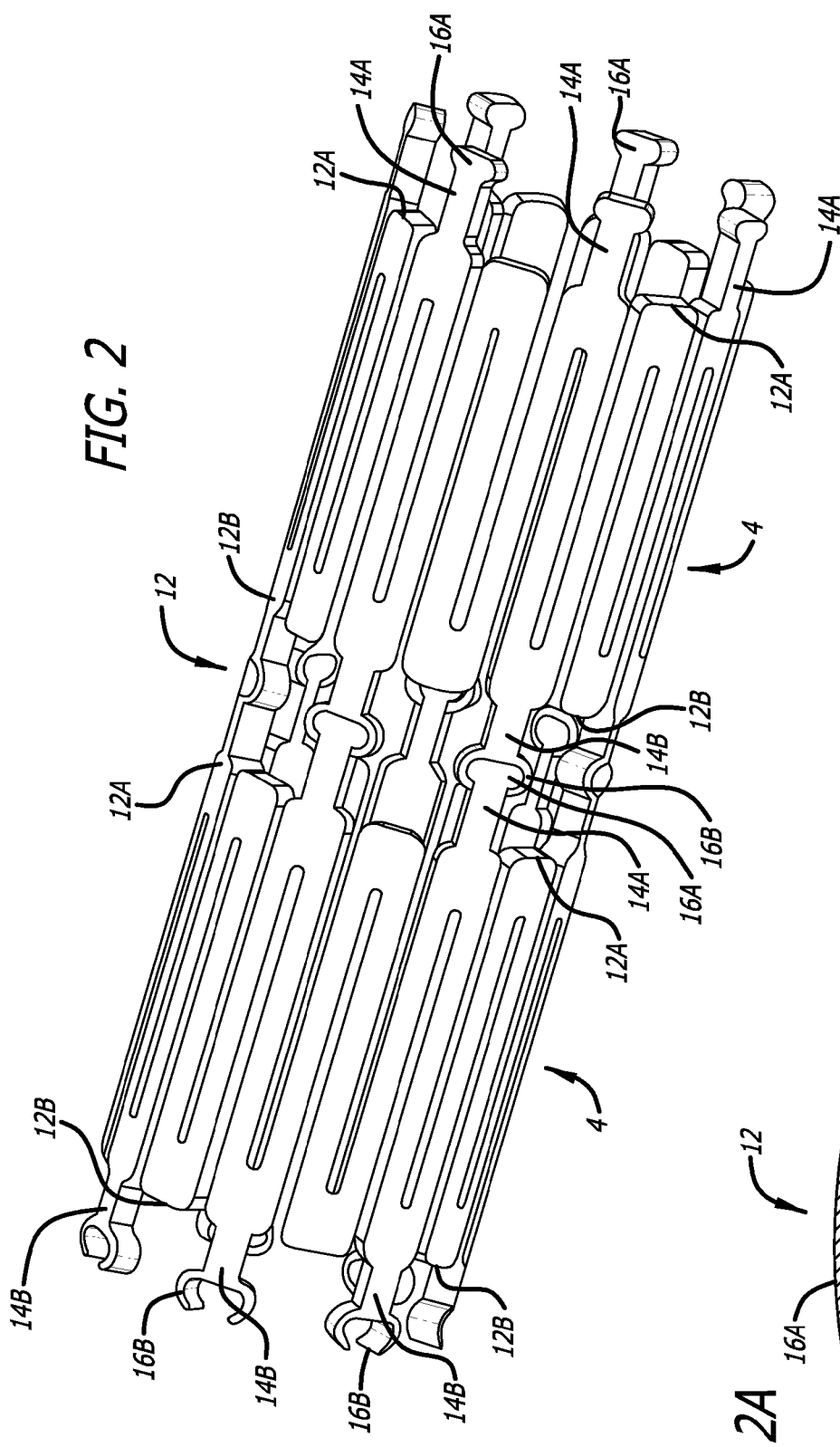
FIG. 2 is a perspective view of two connected meander-shaped stenting rings in their radially small configuration prior to deployment, and showing at respective ends of the meander-shaped rings male and female form-fitting portions to be connected with further such rings.
Figure 2A:
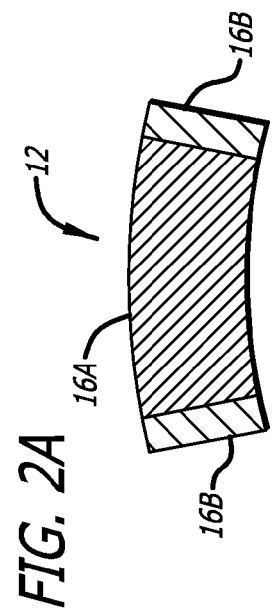
FIG. 2A is a cross-sectional view of connected male and female form-fitting portions, illustrating a frusto-conical shape thereof.

Turning now to FIG. 2, it is shown in more detail how individual rings 4 of the stent tube 2 (FIG. 1) are connected with one another. In contrast to FIG. 1, the stent cylinder is shown in its radially compact disposition. In particular, attention is drawn to the constructional details of the connection points 12, i.e. the bridges connecting the vertices 12A, 12B of two adjacent rings. FIG. 2 illustrates two meander-shaped rings 4, which comprise bridge struts 14A, 14B at both axial ends of each of the rings 4. All of the bridge struts include a straight portion provided for enhancing axial flexibility of the stent tube.

The protruding portions of the bridge struts 14A, 14B can be classified into male portions having an arcuate head portion 16A and female portions having an arcuate recess portion 16B. The female portions comprise rebated internal abutment surfaces to receive the complementary arcuate male head portion. Both male and female portions are frusto-conically shaped due to the laser-cutting process, as described previously. Thus, due to the complementary-shaped male and female portions, they represent a form-fit when connected together which gives the male and female portions excellent attachment security and the bridges are thus self-centering and self-aligning.

Furthermore, the luminal and abluminal major surfaces, out of which the arcuate head portion and the arcuate recess portion are formed, share the same radius of curvature as the major surfaces of the meander-shaped rings. This, however, is not necessarily the case when the stent cylinder is initially laser-cut from flat sheet material.

The number of these mating male and female portions on adjacent meander-shaped rings is not limited to the number shown in FIG. 2. The ratio of mating portions to voids, i.e. points at axial ends of the rings at which the bridge struts 14A, 14B are cut-off during the laser-cutting process, can be as much as 1 to 5, or even 1 to 6 depending on the design of the mesh structure used for the stent. It goes without saying that the number of male portions corresponds to the number of female portions. The number, however, can be readily changed during manufacture of the stent tube.

It has been found that heat generated during the laser-cutting process oxidises part of the metal surface of both male and female form-fitting portions, so that both portions are electrically insulated from one another in the assembled state. This oxide layer provides a portion of reduced or virtually zero electrical conductivity that is effective to improve MRI-imaging of the stent lumen.

The skilled reader will appreciate that other or additional ways of providing reduced conductivity portions intermediate between the two mating portions of two adjacent rings are conceivable, such as immersing either one or both of the mating portions into an oxidising agent or radiating one or both of the mating portions with a laser, thereby generating sufficient heat to oxidise their metal surfaces. It is conceivable that the naturally occurring oxide layer on the surface of the metal stent might be sufficient for providing the conductivity break, especially when the two mating portions are not in physical contact with each other, such that a small gap exists therebetween.

The thickness of the oxide layer depends on the time period and the intensity of the laser used for radiating one of the mating portions. The thickness of this oxide layer should be sufficient that, when the current induced by the external magnetic field exceeds a certain level, a current-breakthrough between two adjacent rings does not occur, so that the quality of the MRI-image of the stent tube will not be deteriorated by artefacts.

Figure 4:
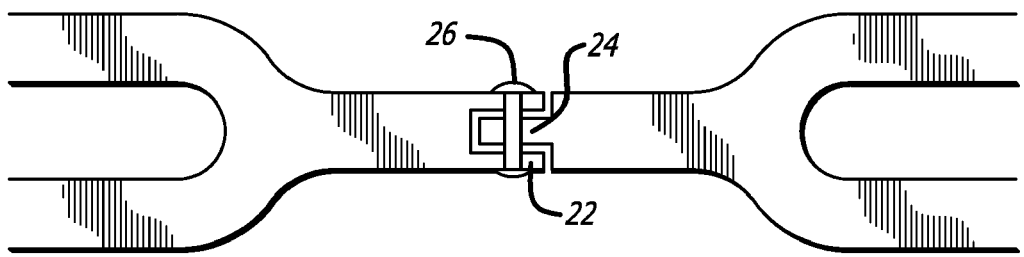
FIGS. 4 to 6 are schematic views of different bridge constructions.

The skilled reader will also appreciate that other ways of connecting two adjacent rings are conceivable. Those alternatives include plug-and-socket type connections, spigot-shoulder type connections, bolt-sleeve type connections, clamped arrangements, glue-type connections, hinge-type connections which further enhance axial flexibility of the stent tube, thread-eyelet type connections in which a thread is fed through respective eyelets at axial ends of the rings and subsequently, the two ends of the thread are knotted to the eyelets of the rings for holding the rings together. It is also conceivable using sleeves for connecting axially protruding bridge struts of two adjacent rings, thereby providing a stent structure in which there is no axial connection of two adjacent rings except by the sleeves (FIG. 4). The sleeves can be made of a material having low electrical conductivity. The protruding bridge struts of two adjacent rings may comprise the shape of a bone structure, i.e. the diameter of the protruding portion increases towards its axial end.

When inserting the male form-fitting portion into the female form-fitting portion, these two portions stay together upon radial expansion of the stent tube solely due to their complementary form-fit. The male portion is inserted into the female portion radially inwardly due to their radially tapered shape, so that upon radial expansion of the stenting rings, the female portion can push the male portion radially outwardly, thereby pressing the male head portion further inwardly into the female recess portion against the rebated internal abutment surface of the female portion. Friction between the complementary male and female portions may help to improve the rigidity of the connection. See above mentioned WO 02/15820. However, this effect is more amenable to application in balloon-expandable stents, than it is in self-expandable stents. In self-expandable stents, upon deployment of the stent by proximal progressive withdrawal of an outer confining sheath, the angle between the released and unreleased portion of the stent can be large enough to spring the male-female bridge strut engagement apart, at the moment of release from the sheath.

A biocompatible adhesive, although not necessary, may be used to permanently attach two adjacent rings with one another. If the biocompatible adhesive is moreover non-conductive, the extra oxide layer created by, e.g. immersing at least one of the ends of the two complementary form-fitting portions into an oxidising agent, may be omitted. Suitable adhesives may include polymeric based adhesives, such as parylene, acrylate, silicone, PTFE, and stable or biodegradable adhesives. An example of biodegradable adhesives includes lactide acids. Biodegradable adhesives are thought of being advantageous in that they render the stent structure more flexible after deployment and once the process of bio-degradation has started. It is also contemplated coating the axially protruding bridge struts with a non-conductive coating. Suitable coatings include diamond-like carbon (DLC) coatings, SiC, $SiO_2$ or ceramic coatings.

Linkage between two adjacent rings via connecting two bridge struts facing each other can be obtained by using the adhesive or coating itself as the linking member, or by bringing the bridge struts in close proximity with each other so that a gap remains therebetween, e.g. using a sleeve, thereby ensuring that no direct contact between the bridge ends is established, neither within nor outside of the sleeve. However, the latter does not exclude that an adhesive or coating is applied to the thus connected bridge ends.

Methods of applying an adhesive and/or coating include physical vapor deposition (PVD), implantation, injection, dipping, welding, soldering, brazing, plasma deposition, flame-spraying etc.

The skilled person, however, will appreciate that other adhesives and coatings, and methods of applying them, are conceivable.

The junction between two adjacent stenting rings, or even the adhesive or coating itself, may be used as a carrier for drugs inhibiting restenosis. The drugs can be incorporated into the adhesive and/or coating, and will be released therefrom in a dosed manner, so that restenosis is prevented from occurring inside the lumen of the stent.

Figure 3:
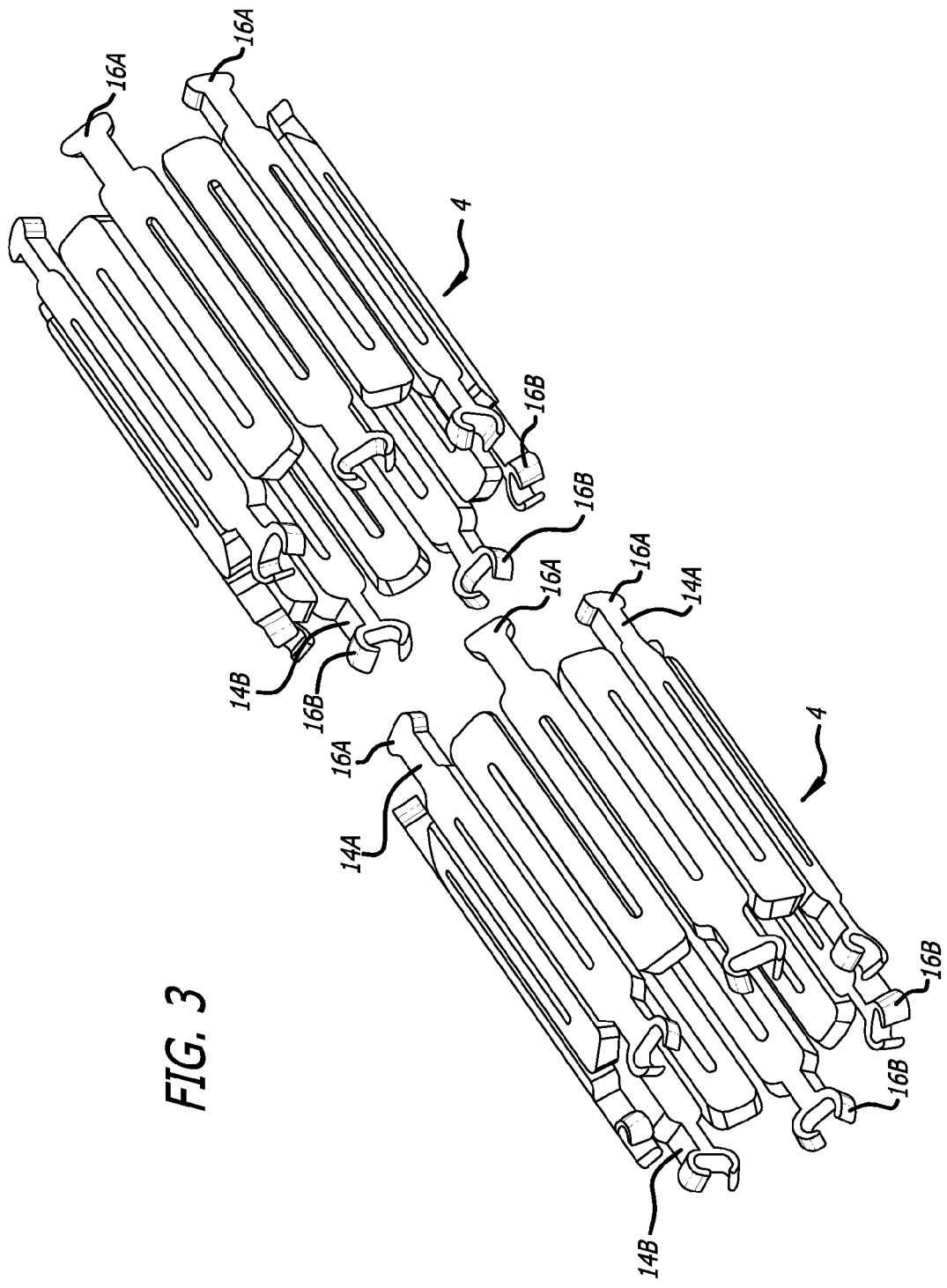
FIG. 3 is a perspective view of the two meander-shaped rings shown in FIG. 2 separated from each other.

Turning now to FIG. 3, the two stenting rings are illustrated in the disassembled state. As can be seen, the two male and female complementary form-fitting portions are capable of snugly fitting together with the portion of reduced conductivity in between. The luminal surface of the bridges 12 is flush with the luminal surface of the stenting rings. This, however, is not crucial for carrying the inventive concept into effect. The luminal surface of the bridges may well be located radially inwardly with respect to the luminal surface of the stenting rings. However, in order to provide unobstructed fluid flow through the stent lumen, the luminal surfaces of the bridges should preferably be flush with the luminal surfaces of the rings.

FIG. 4 shows a connecting bridge between two connected stenting rings with male and female complementary form-fitting portions forming the bridge between two stenting rings according to another preferred embodiment of the invention. The female form-fitting portion has the shape of a fork 22 receiving the male form-fitting portion 24 within the recess in the centre of the fork. Due to the laser cutting process, both male and female form-fitting portions are frusto-conically shaped. There is a gap between the male and female form-fitting portion. If a laser is used for cutting, the size of the male and female form-fitting portions essentially corresponds to the dimension of the laser beam focus. The male and female form-fitting portions can be produced, however, separately, in which case the gap therebetween may differ from the dimension of the laser focus. This gap accounts for enhanced flexibility of this type of structure. A laser-drilled through-hole extends through the male and female form-fitting portions such that both through-holes are in line in order to allow a pin 26 to be inserted therethrough for fixation of the male form-fitting portion to the female form-fitting portion. The through-holes can be created by a laser beam drill, either under manual control under a microscope, or automatically under microprocessor control. Preferably, the pin has a surface made of an electrically-insulating material, such as an oxide layer. It is also contemplated to use pins 26 fabricated entirely from non-conductive material, such as polymeric based materials, ceramics, etc.

Figure 5:
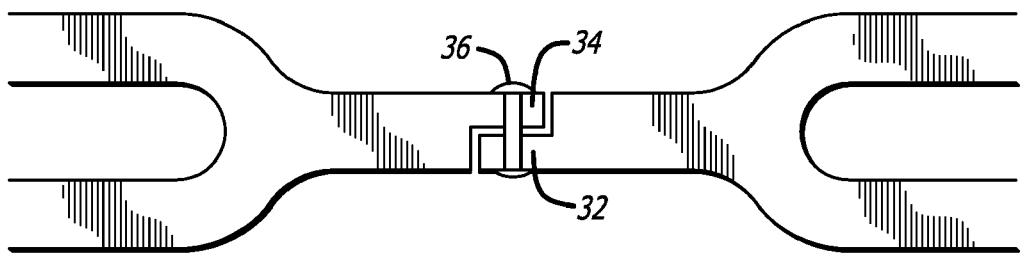

FIG. 5 shows another preferred embodiment of the bridge of the invention. Two stenting rings are connected via mating portions 32, 34 both that are complementary in shape and have a through-hole through which a pin 36 can be inserted so that the bridge functions as a hinge joint. Again, due to the laser beam focus having a finite width, a gap remains between the two complementary portions when connected, so that the connection allows a certain degree of pivotal movement when the stent tube is advanced along a tortuous path inside a body vessel.

Each hinge pin 26, 36 may be mechanically fixed to the respective ends of the two complementary mating portions, such as by glueing, or may be fixed in some other way. Again, the cylindrical surface of the pin is preferably electrically-insulating.

Figure 6:
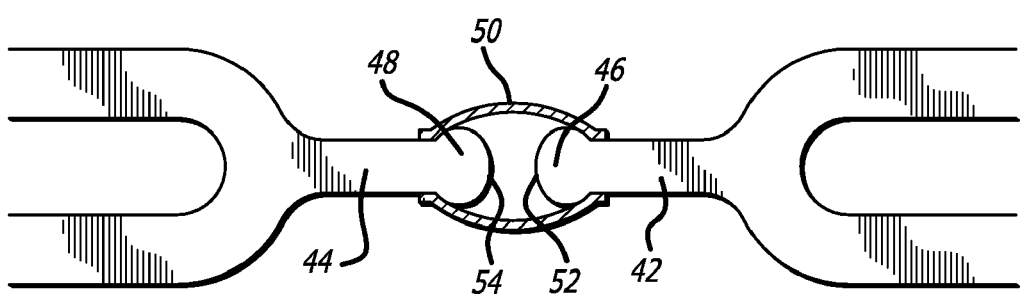
Figure 7:
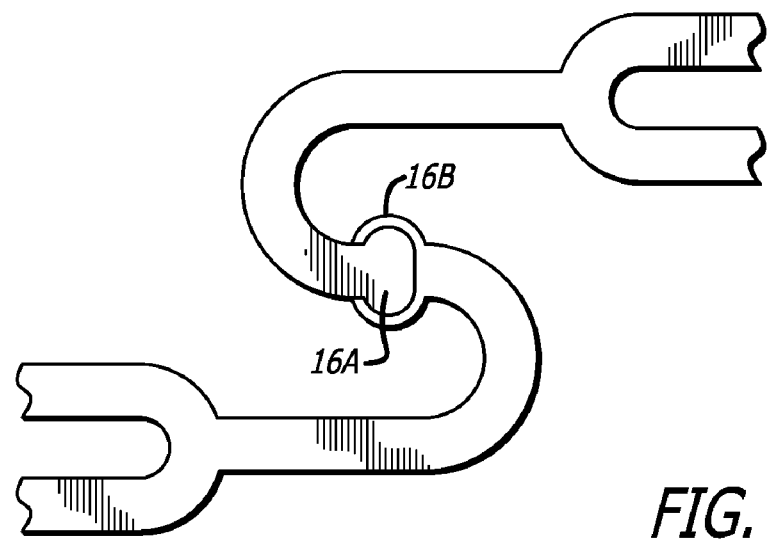
FIG. 7 is a schematic view of a bridge with a shape that resembles an "S"
Figure 8:
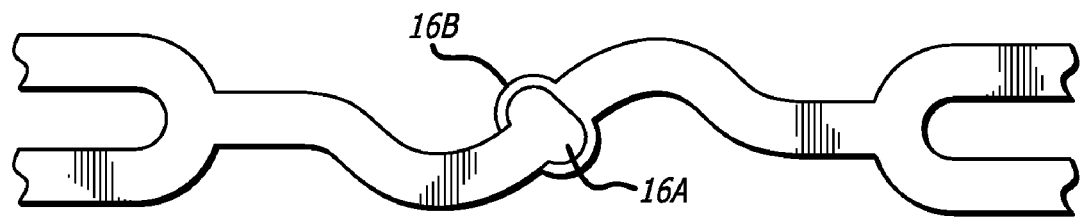
FIG. 8 is a schematic view of a bridge with a shape that resembles a meander.

FIG. 6 shows bridge struts 42, 44 provided with a bulbous cantilever end, 46, 48 respectively, and surrounded by a shrink sleeve 50. Each of the bulbous ends is treated to provide it with an insulating oxide layer 52, 54. The bridge functions somewhat like a knee joint.

In order to complete the entire stent cylinder, a plurality of such stenting rings is connected in series. Since every bridge comprises a portion of reduced electrical conductivity, there is no unimpeded electrical connection running from one end of the stent cylinder to the other. Due to the highly resistive connections between adjacent rings, the desired effect is achieved, so that, when the stent cylinder is exposed to an HF-signal in a MRI-imaging apparatus, the incidence of artefacts on the MRI-image of the stent lumen is reduced.

Once the stent cylinder is completed by connecting a plurality of such stenting rings in series, and the stent cylinder is confined within an outer sheath ready for deployment, the structure of the stent cylinder, and in particular the structure of the bridges, according to one preferred embodiment, as shown in FIG. 3, allows placement of individual stenting sections at spaced-apart locations inside a body vessel. This is accomplished by gradually moving the outer sheath proximally by an amount equal to the axial length of one stenting ring. This enables the medical practitioner to release only one stenting ring at a time so that individual stenting rings separated by bridges can be placed at different locations within the lumen of a body vessel. It is clear to the skilled person that the structure of the bridge has to be such that one stenting ring can separate itself from its neighbouring stenting ring whilst the neighbouring stenting ring is still confined within the outer sheath.

The term "portion of reduced or virtually zero electrical conductivity" is to be construed such that the electrical conductivity of that portion between two bridge struts facing each other on two adjacent rings is substantially less, i.e. at least an order of magnitude lower, than the electrical conductivity of the stenting rings. Ideally, no electrical continuity exists between two adjacent rings, and therefore between the two axial ends of the stent, but in reality there must inevitably be some residual conductivity.

It is also contemplated that the portion of reduced conductivity can be entirely, or at least in part, created by modifying the chemical composition of the abutment surfaces of the protruding struts of the metal structure. Modifying the chemical composition can be achieved by doping, ion beam epitaxy, ion bombardment, etc., all of which result in a modified electrical conductivity of the surface portion of the metal structure exposed to such treatment.

Arranging the bridge length non-parallel to the stent length can increase the bridge length relative to the spacing between the two adjacent stent rings connected by the bridge, and this extra length may be useful, if the bridge is made electrically non- or poorly-conductive, to enhance electrical isolation between adjacent rings.

Further bridge design possibilities to improve visibility of the stent lumen by MRI may include:

locally reduced bridge cross-sectional area;

a deep meander within the bridge length, to create anti-parallel bridge length portions which influence the electrical performance of the bridge element in an HF field such as is present during MRI procedures;

modifications to the surface of the bridge, to capitalise on skin effects which manifest themselves in an HF field and change the electrical performance of the element that defines the surface;

creating within the bridge induction-related or resonance-related electro-magnetic effects, possibly by judicious selection of specific ring structures for combination with specific bridge structures, and particular locations of the bridges with respect to the rings.

The skilled person will appreciate that, although the invention is primarily directed to tubular radially expansible metal structures, such as stents, it may also be applied to guide wires used in catheter-based surgery. Such guide wires may also be provided with dielectric or non-conductive intermediate portions along the actual length of the guide wire. It is thought that providing a conductivity break at least every 20 cm along the distal part of the guidewire length will allow the guidewire to merit the designation "MRI-compatible".

The scope of protection of the claims which follow is not to be limited to the embodiments described in detail above. Readers will appreciate that the detailed description is to assist the skilled reader in realising embodiments within the scope of the claims rather than to set a limit on the scope of protection.

The invention claimed is:

1. A tubular radially expansible metal structure, comprising:
 a wall comprising an abluminal major wall surface, a luminal major wall surface and a radial wall thickness therebetween, the wall having struts defining through-apertures therein; and
 a plurality of expansible rings arranged adjacent one another along a longitudinal axis of the structure, each of the rings defining at least one bridge strut and each of the rings having a first electrical conductivity, adjacent rings linked by at least one bridge formed by cooperation between adjacent bridge struts on adjacent rings;
 each bridge including a portion having a second electrical conductivity at least an order of magnitude lower than the first electrical conductivity, the bridges distributed throughout the length of the tubular structure and configured and arranged to divide the tubular structure into axially spaced and electrically insulated sections.

2. The structure according to claim 1, wherein said bridge comprises inter-engaged joint portions.

3. The structure according to claim 1, wherein said bridge comprises complementary mating portions.

4. The structure according to claim 3, wherein the mating portions are male-female form-fitting portions.

5. The structure according to claim 4, wherein the form-fitting portions have a frusto-conical shape.

6. The structure according to claim 4, wherein the male form-fitting portion comprises a mating head portion having an arcuate end surface, and the female form-fitting portion comprises a mating arcuate end portion with a rebated internal abutment surface to receive the arcuate head portion.

7. The structure according to claim 3, wherein at least one of the mating portions carries a biocompatible adhesive for enhancing the rigidity of said bridge.

8. The structure according to claim 3, wherein a portion of reduced electrical conductivity comprises a conductivity reducing layer on an abutment surface of at least one of the complementary mating portions.

9. The structure according to claim 1, wherein a portion of reduced electrical conductivity comprises a portion in which the chemical composition of said metal structure is modified.

10. The structure according to claim 1, wherein a portion of reduced electrical conductivity comprises an oxide layer.

11. The structure according to claim 1, wherein said bridges comprise a sleeve connected to adjacent bridge struts, and wherein said bridge struts are spaced apart within said sleeve.

12. The structure according to claim 1, wherein the longitudinal axis of said bridge is not parallel to the longitudinal axis of the structure.

13. The structure according to claim 1, wherein said bridge has the shape of a meander.

14. The structure according to claim 1, wherein the rings have the shape of a meander.

15. The structure according to claim 14, wherein the number of bridges connecting one ring with an adjacent ring is less than the number of meanders in one ring.

16. The structure according to claim 1, wherein the shape of the bridge resembles that of an "S".

17. The structure according to claim 1, wherein the structure is made of a nickel titanium shape-memory alloy.

18. The structure according to claim 1, wherein the structure is made of stainless steel.

19. The structure according to claim 1, wherein the structure is a medical stent.

20. A method of manufacturing a tubular radially expansible metal structure having an abluminal major wall surface, a luminal major wall surface and a radial wall thickness therebetween, comprising the steps of:
 forming a plurality of expansible rings so that the rings are arranged adjacent one another along the longitudinal axis of the structure, each of the rings defining at least one bridge strut and each of the rings having a first electrical conductivity;
 forming bridges between adjacent rings by approximating respective bridge struts of adjacent rings; and
 furnishing said bridges between each ring and its adjacent ring with a portion having a second electrical conductivity at least an order of magnitude lower than the first electrical conductivity, the bridges distributed throughout the length of the tubular structure, arranged and configured to divide the tubular structure into axially spaced and electrically insulated sections.

21. The method according to claim 20, wherein the step of forming the expansible rings further comprises the steps of:
 providing a tubular workpiece;
 mounting the tubular workpiece on a support; and
 laser-cutting the workpiece to form meanders in the rings arranged longitudinally adjacent one another, each having a first end and a second end, and at least one complementary mating portion arranged on said first end of each of said rings to mate with a complementary mating portion on the second end of an adjacent ring.

22. The method according to claim 21, wherein the tubular workpiece has a longitudinal axis of rotation and the direction of the laser cutting beam when cutting the workpiece intersects said longitudinal axis.

23. The method according to claim 21, wherein the direction of the laser cutting beam for making the bridge struts departs from a direction which intersects said longitudinal axis.

24. The method according to claim 20, wherein the step of linking each of the rings with an adjacent ring by at least one bridge includes the step of oxidizing abutment surfaces on said bridge struts, whereby each bridge includes a conductivity reducing layer which constitutes a portion of reduced conductivity.

25. The method according to claim 20, wherein the step of linking each of the rings with an adjacent ring by at least one bridge includes the steps of:
 providing an insulating sleeve; and
 mounting said sleeve to adjacent bridge struts on adjacent rings, such that the bridge struts are spaced apart within said sleeve.

26. The method according to claim 21, wherein the furnishing step includes generating sufficient heat during the laser-cutting step such that the complementary mating portions are electrically insulated from one another in an assembled state.

27. The method according to claim 21, wherein the furnishing step comprises immersing at least one of the complementary mating portions into an oxidizing agent.

28. The method according to claim 21, wherein the furnishing step comprises radiating at least one of the complementary mating portions with a laser.

29. The structure according to claim 1, wherein the adjacent bridge struts include complementary mating portions spaced apart by a gap.

30. The structure according to claim 1, further comprising a pin inserted in a through-hole formed in each of the adjacent bridge struts.

31. The structure according to claim 30, wherein the pin has a surface made of an electrically insulating material.

32. The structure according to claim 31, wherein the electrically insulating material comprises an oxide layer.

33. The structure according to claim 30, wherein the pin is formed of a non-conductive material.

34. The structure according to claim 33, wherein the non-conductive material is one of a polymeric based material and a ceramic material.

35. The structure according to claim 30, wherein the pin is fixed to each of the adjacent bridge struts.

* * * * *